United States Patent
Camargo Amado et al.

(10) Patent No.: US 10,603,381 B2
(45) Date of Patent: Mar. 31, 2020

(54) SYNTHESIS OF NANOCOMPOUNDS COMPRISING ANATASE-PHASE TITANIUM OXIDE AND COMPOSITIONS CONTAINING SAME FOR THE TREATMENT OF CANCER

(71) Applicant: UNIVERSIDAD DEL VALLE, Cali (CO)

(72) Inventors: Rubén Jesús Camargo Amado, Cali (CO); José Oscar Gutiérrez Montes, Cali (CO); Mónica Jimena Basante Romo, Cali (CO); William David Criollo Gómez, Cali (CO)

(73) Assignee: Universidad del Valle (CO)

( * ) Notice: Subject to any disclaimer, the term of this patent is extended or adjusted under 35 U.S.C. 154(b) by 17 days.

(21) Appl. No.: 15/511,222

(22) PCT Filed: Feb. 17, 2015

(86) PCT No.: PCT/IB2015/051143
§ 371 (c)(1),
(2) Date: Mar. 14, 2017

(87) PCT Pub. No.: WO2016/055869
PCT Pub. Date: Apr. 14, 2016

(65) Prior Publication Data
US 2017/0281770 A1    Oct. 5, 2017

(30) Foreign Application Priority Data
Oct. 10, 2014    (CO) .................................. 14-225737

(51) Int. Cl.
*A61K 31/28* (2006.01)
*A61N 5/06* (2006.01)
(Continued)

(52) U.S. Cl.
CPC ............ *A61K 41/00* (2013.01); *A61K 9/0092* (2013.01); *A61K 9/5123* (2013.01); *A61K 31/28* (2013.01);
(Continued)

(58) Field of Classification Search
None
See application file for complete search history.

(56) References Cited

U.S. PATENT DOCUMENTS

| 2008/0242785 A1* | 10/2008 | Ma .................. | B82Y 30/00 |
| | | | 524/413 |
| 2009/0175757 A1* | 7/2009 | Yao .................. | C04B 41/009 |
| | | | 422/4 |

FOREIGN PATENT DOCUMENTS

CN            102292291 A   * 12/2011   ............. B82Y 10/00

OTHER PUBLICATIONS

Author Unknown. English Translation of CN 102292291 A. Downloaded from https://patents.google.com/patent/CN102292291A/en?oq=multi-walled+carbon+nanotubes+TiO2 on Apr. 25, 2018. Originally published Dec. 21, 2011. 7 printed pages. (Year: 2011).*

(Continued)

*Primary Examiner* — Isaac Shomer
(74) *Attorney, Agent, or Firm* — Joseph L. Morales; The Morales Law Firm

(57) ABSTRACT

This invention relates to novel nanocompounds that are cytotoxic to tumor cells when combined with ultraviolet light, the nanocompounds comprising multilayered carbon nanotubes with anatase-phase titanium dioxide or anatase-phase titanium dioxide and folate. The invention also relates to a composition containing said nanocompounds and to a method for the treatment of cancer; comprising the administration of said composition in co-treatment with UV radia- (Continued)

tion. The invention further relates to a method for the synthesis of the nano-compounds.

6 Claims, 3 Drawing Sheets

(51) Int. Cl.
    C07F 7/28      (2006.01)
    B82Y 5/00      (2011.01)
    A61K 41/00     (2020.01)
    A61K 9/51      (2006.01)
    A61K 9/00      (2006.01)
    A61K 47/69     (2017.01)
    A61K 47/55     (2017.01)

(52) U.S. Cl.
    CPC ...... *A61K 41/0038* (2013.01); *A61K 41/0057* (2013.01); *A61K 47/551* (2017.08); *A61K 47/6923* (2017.08); *A61K 47/6925* (2017.08); *A61K 47/6929* (2017.08); *A61N 5/062* (2013.01); *C07F 7/28* (2013.01); *A61N 2005/0661* (2013.01); *B82Y 5/00* (2013.01); *Y10S 977/773* (2013.01)

(56) References Cited

OTHER PUBLICATIONS

S Abbasi, SM Zebarjad, SHN Baghban. "Decorating and Filling of Multi-Walled Carbon Nanotubes with TiO2 Nanoparticles via Wet Chemical Method." Engineering, vol. 5, 2013, pp. 207-212. (Year: 2013).*

S Aryal, CK Kim, K-W Kim, MS Khil, HY Kim. "Multi-walled carbon nanotubes/TiO2 composite nanofiber by electrospinning." Materials Science and Engineering C, vol. 28, 2008, pp. 75-79. (Year: 2008).*

X-H Xia, Z-J Jia, Y Yu, Y Liang, Z Wang, L-L Ma. "Preparation of multi-walled carbon nanotube supported TiO2 and its photocatalytic activity in the reduction of CO2 with H2O." Carbon, vol. 45, 2007, pp. 717-721. (Year: 2007).*

Y Zhao, Y Hu, Y Li, H Zhang, S Zhang, L Qu, G Shi, L Dai. "Super-long aligned TiO2/carbon nanotube arrays." Nanotechnology, vol. 21, 2010, pp. 1-7. (Year: 2010).*

M Adeli, R Soleyman, Z Beiranvand, F Madani. "Carbon nanotubes in cancer therapy: a more precise look at the role of carbon nanotube-polymer interactions." Chemical Society Reviews, vol. 42, 2013, pp. 5231-5256. (Year: 2013).*

JM Ngoy, SE Iyuke, WE Neuse, CS Yah. "Covalent Functionalization for Multi-walled Carbon Nanotube (f-MWCNT)-Folic Acid Bound Bioconjugate." Journal of Applied Sciences, vol. 11(15), 2011, pp. 2700-2711. (Year: 2011).*

W Wang, P Serp, P Kalck, JL Faria. "Photocatalytic degradation of phenol on MWNT and titania composite catalysts prepared by a modified sol-gel method." Applied Catalysis B: Environmental, vol. 56, 2005, pp. 305-312. (Year: 2005).*

S Wang, S Zhou. "Photodegradation of methyl orange by photocatalyst of CNTs/P-TiO2 under UV and visible-light irradiation." Journal of Hazardous Materials, vol. 185, 2011, pp. 77-85. (Year: 2011).*

D-Q Yang, J-F Rochette, E Sacher. "Functionalization of Multiwalled Carbon Nanotubes by Mild Aqueous Sonication." Journal of Physical Chemistry B, vol. 109, 2005, pp. 7788-7794. (Year: 2005).*

J Li, D Kuang, Y Feng, F Zhang, M Liu. "Glucose biosensor based on glucose oxidase immobilized on a nanofilm composed of mesoporous hydroxyapatite, titanium dioxide, and modified with multi-walled carbon nanotubes." Microchim Acta, vol. 176, 2012, pp. 73-80. (Year: 2012).*

R Li, R Wu, L Zhao, Z Hu, S Guo, X Pan, H Zou "Folate and iron difunctionalized multiwall carbon nanotubes as dual-targeted drug nanocarrier to cancer cells." Carbon, vol. 49, 2011, pp. 1797-1805. (Year: 2011).*

SC Tilton et al. "Three human cell types respond to multi-walled carbon nanotubes and titanium dioxide nanobelts with cell-specific transcriptomic and proteomic expression patterns." Nanotoxicology, vol. 8(5), Aug. 2014, pp. 533-548. (Year: 2014).*

Chen et al., Enhanced photocatalytic activities of TiO2-reduced graphene oxide nanocomposites controlled by Ti—O—C interfacial chemical bond, Materials Research Bulletin (2018) 99:29-36.

Karousis and Tagmatarchis, Current Progress on the Chemical Modification of Carbon Nanotubes, Chem. Rev. (2010) 110:5366-5397.

Kesharwani et al., Carbon nanotube exploration in cancer cell lines, Drug Discovery Today (2012) 17 (17/18):1023-1030.

Reddy and Ramaprabhu, Nanocrystalline Metal Oxides Dispersed Multiwalled Carbon Nanotubes as Supercapacitor Electrodes, J. Phys. Chem. C. (2007) 111:7727-7734.

Wong et al., Carbon nanotubes for delivery of small molecule drugs, Advanced Drug Delivery Reviews, (2013) 65:1964-2015.

* cited by examiner

SYNTHESIS OF NANOCOMPOUNDS COMPRISING ANATASE-PHASE TITANIUM OXIDE AND COMPOSITIONS CONTAINING SAME FOR THE TREATMENT OF CANCER

FIELD OF THE INVENTION

The present invention is related to a novel nanocompound that comprises multilayered carbon nanotubes and anatase phase titanium dioxide ($TiO_2$), the synthesis process of said nano-compound, a composition containing said nano-compound, and a method for cancer treatment that comprises administration of a therapeutically effective amount of said nano-compound and irradiation with UV-A light of cancerous tissue.

BACKGROUND OF THE INVENTION

Carbon nanotubes have shown great potential in the biomedical field, particularly in areas of tissue engineering, thermal ablation (photo-thermal and photo-acoustic therapy) and in the development of drug release systems. This last application has permitted developing controlled and directed release systems of different drugs that range from small molecules to peptides and antibodies; these systems permit increasing the pharmacological activity of the drugs and diminishing the collateral effects associated to them due, in part, to the effect of permeability and retention that permits accumulating these nano-compounds in tumor tissues, and the pin shape of the nanotubes that facilitates penetration through these membranes and intra-cellular accumulation of the drug (Wong, B. S., et al., Advanced Drug Delivery Reviews 65 (2013):1964-2015).

Functionalization of the nanotubes permits improving solubility in aqueous media, reducing cytotoxicity, and generating additional sites to add other molecules for the purpose of bio-redirecting or imaging (Kesharwani, P., et al., Drug Discovery Today 17 (2012):1023-1030). This functionalization can be covalent by modifying the nanotube structure with hydrophilic functional groups or non-covalent by coating with macromolecules, like lipids, polymers, or surfactants (Wong, B. S., et al., Advanced Drug Delivery Reviews 65 (2013) 1964-2015).

In the field of chemotherapy, different nano-compounds have been evaluated for release of cytotoxic drugs, for example, multilayered nanotubes functionalized with triethylene glycol diamine or PVA and loaded with camptothecin, mono-layered nanotubes functionalized with PEG or folic acid conjugated to chitosan and loaded with doxorubicin.

Other documents revealed by the state-of-the-art and related to nano-compounds for drug release are discussed ahead:

Patent Application Publication No. US2010209479 reveals a composition for cancer treatment that comprises a multilayered carbon nanotube and at least one therapeutic agent disposed within the nanotube, where the nanotube has a length between 500 nm and 2 µm and is coated with a polymer material selected from alginate, PLGA, polylactic acid, polydecanodiol citrate, and combinations of the same. Where the therapeutic agent is selected from xaliplatin and mitomycin and is present in a concentration between 1 and 300 µM. The patent reveals a treatment method that comprises placing said composition in contact with cancerous tissue and accelerating the reuptake of the therapeutic agent through localized irradiation with electromagnetic radiation for a time below 10 seconds.

Document US2007202334 reveals a nanomaterial that comprises anatase phase titanium dioxide in Nano fiber form with a length of at least 2 µm and diameter between 0.5 and 3 nm. Said nanofiber comprises at least a doping metal or non-metal selected from calcium, cobalt, nickel, copper, gallium, strontium, zirconium, palladium, silver, platinum, boron, carbon, nitrogen, sulfur, or fluorine among others. Likewise, the document reveals a catalytic composition that comprises anatase phase titanium dioxide nanoparticles, which in combination with irradiation of visible light reduce the percentage of organic substance or the viability of bacteria.

Document US2014155333 divulges a method for cancer treatment that comprises administration of: (a) a carbon nanotube-protein complex, where said nanotube is single-wall type (SWNT) semiconductor and non-metallic, where the protein or peptide is bonded to the SWNT through a derivate of the cellulose and is capable of recognizing a receptor of an ion of the endothelial tumor vasculature or of the external surface of these tumor cells; (b) electromagnetic radiation in a wavelength absorbable by the SWNT that generates increased temperature of the nanotube-protein complex and causes damage or death of said tumor cell.

In spite of the development of different nano-compounds, both single- and multi-layered, which incorporate drugs or proteins in their interior or bonded to the surface that permit increasing cytotoxicity and diminishing collateral effects, the need exists to develop new selective cytotoxic nano-compounds that in co-treatment with ionizing radiations permit eliminating tumor cells without the deleterious effects of the chemo and/or conventional radiotherapy on non-tumor cells. The nano-compounds of the present invention that comprises functionalized multi-walled carbon nanotubes with groups and Anatase phase $TiO_2$ ($TiO_2$-FMWCNTs) and functionalized multi-walled carbon nanotubes, Anatase phase $TiO_2$ and folate ($TiO_2$-FMWNTs-Folate) are cytotoxic against tumor cells, while not inducing cytotoxic effects upon normal cells; are not genotoxic or mutagenic and in combination with UV-A-type radiation increase cytotoxicity against tumor cells becoming an alternative to solving the errors of the nano-compounds divulged previously.

BRIEF DESCRIPTION OF THESE FIGURES

Figure 3:
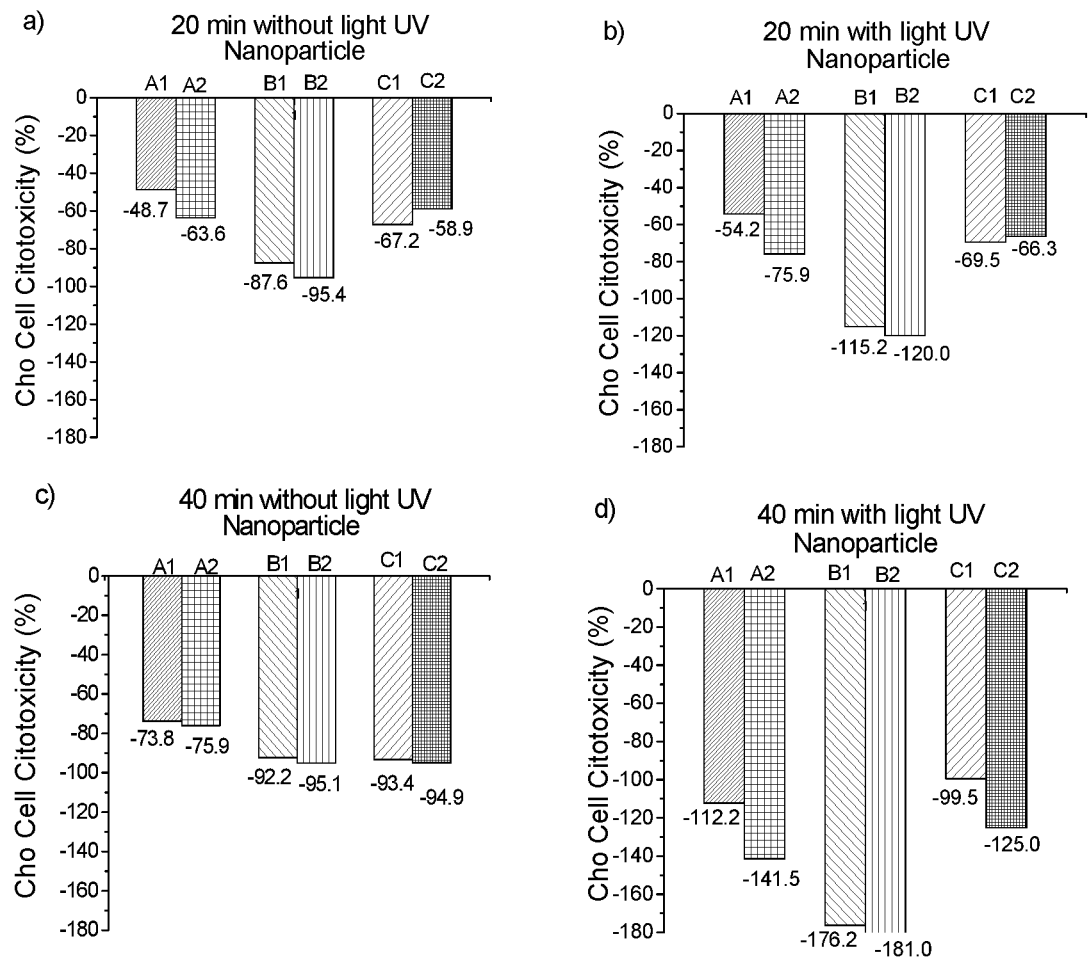

FIG. 3 presents the lack of cytotoxicity of the nano-compounds upon normal Chinese hamster ovary (CHO) cells. a) 20 min without UV, b) 20 min with UV, c) 40 min without UV, d) 40 min with UV.

OBJECTS OF THE INVENTION

In a first object, the invention is related to the synthesis of a nano-compound that comprises functionalized multi-walled carbon nanotubes and Anatase phase $TiO_2$ ($TiO_2$-FMWNTs).

In a second object, the invention reveals a nano-compound that comprises functionalized multi-walled carbon nanotubes, Anatase phase $TiO_2$, and folate ($TiO_2$-FMWNTs-Folate).

In a third object, the invention reveals a composition containing the nano-compounds and a pharmaceutically acceptable diluent.

In an additional object, the invention reveals a method for cancer treatment that comprises administration of a therapeutically effective amount of a nano-compound and irradiation of cancerous tissue with UV-A light.

DETAILED DESCRIPTION OF THE INVENTION

In a first object, the invention divulges a synthesis process of a nano-compound that comprises functionalized multi-walled carbon nanotubes and Anatase phase $TiO_2$ (FMWCNTs) that comprises the stages of:
  a) Dispersing in anhydrous $C_{1-4}$ alcohol between 1 and 5 wt % of functionalized multi-walled carbon nanotubes (FMWCNTs), with diameters of 20 to 30 nm, length of 10 to 30 µm, ash content below 1.5% in an ultrasonic bath for a time of between 1 and 5 min at temperature between 10 and 20° C. Where said nanotubes are in a proportion between 1 and 5% p/p with purity higher than 90%.
  b) Adding titanium tetrabutoxide (Ti(OBu)$_4$) 99% purity and agitating for 1 to 5 min at a temperature of between 10 and 20° C.
  c) Adding deionized distilled water at a rate of between 10 and 20 ml/min to obtain an ethanol:water solution with a composition in volume between 70 and 90% of ethanol and 10 to 30% of water.
  d) Allowing the solution to rest in a desiccator at a temperature of between 10 and 20° C. for 24 to 96 h to permit the condensation reaction.
  e) Subjecting the material to heating at a rate of between 0.01 to 0.1° C./min to a temperature of between 100 and 250° C. for 1 to 3 h.
  f) Heating the material at a rate of between 0.01 to 0.1° C./min to a temperature of between 450 and 550° C. and maintaining this temperature for 1 to 3 h.
  g) Cooling the material to a temperature of between 10 and 20° C. at a rate of between 100 to 150° C./min.

In an additional aspect, the invention reveals a nano-compound that comprises functionalized multi-walled carbon nanotubes, Anatase phase $TiO_2$ and folate ($TiO_2$-FMWNTs-Folate) that comprises the stages of:
  a) Mixing dicyclohexylcarbodiimide and N-hydroxysuccinimide in a 1:1 ratio at a concentration of 0.01 to 0.1 M in DMSO for a time of between 3 and 7 min in ultrasound equipment.
  b) Adding to the mixture functionalized multi-walled carbon nanotubes (FMWCNTs) obtained in the previous process in a proportion of between 1 and 5 parts per part of the mixture from stage (a) and shaking in ultrasonic bath for a time of between 30 and 90 min at a temperature of between 10 and 20° C.
  c) Adding folic acid in a proportion of between 0.01 and 0.1 parts for one part of the functionalized multi-walled carbon nanotubes (FMWCNTs) and shaking in an ultrasonic bath for a time of between 30 and 60 min at a temperature of between 10 and 20° C.
  d) Centrifuging at between 800 and 1200 rpm for a time of between 30 and 60 min at a temperature of between 10 and 20° C. and removing the supernatant.
  e) Heating the material at a rate of between 1 to 5° C./min to a temperature of between 75 and 150° C. and maintain this temperature during 30 to 90 min, to, thus, obtain functionalized multi-walled carbon nanotubes-Folate (FMWCNTs-Folate).
  f) Dispersing in an anhydrous $C_{1-4}$ alcohol of between 1 and 5 wt % of functionalized multi-walled carbon nanotubes-Folate (FMWCNTs-Folate), with diameters from 20 to 30 nm, length from 10 to 30 µm, ash content below 1.5% in ultrasonic bath for a time of between 1 and 5 min at a temperature of between 10 and 20° C. Where said nanotubes are in a proportion of between 1 and 5% p/p with purity above 90%.
  g) Adding titanium tetrabutoxide (Ti(OBu)$_4$) of 99% purity and shaking for 1 to 5 min at a temperature of between 10 and 20° C.
  h) Adding deionized distilled water at a rate of between 10 and 20 ml/min to obtain an ethanol:water solution with a concentration of between 70 and 90% in volume of ethanol and 10 to 30% of water.
  i) Allowing the solution to rest in a desiccator at a temperature of between 10 and 20° C. for 24 to 96 h to permit the condensation reaction.
  j) Subjecting the material to heating at a rate of between 0.01 and 0.1° C./min to a temperature of between 100 and 250° C. for 1 to 3 h
  k) Heating the material at a rate of between 0.01 to 0.1° C./min to a temperature of between 450 and 550° C. and maintaining this temperature for 1 to 3 h.
  l) Cooling the material to a temperature of between 10 and 20° C. at a rate of between 100 to 150° C./min.

These nano-compounds comprising functionalized multi-walled carbon nanotubes and Anatase phase $TiO_2$ (FMWCNTs) and functionalized, Anatase phase $TiO_2$ and folate ($TiO_2$-FMWNTs-Folate) are cytotoxic against tumor cells in co-treatment with UV-A ultraviolet light, while not inducing cytotoxic effects upon normal cells with or without UV-A ultraviolet light co-treatment. Said cytotoxicity against tumor cell lines is evidenced in treatment times below 60 min and in synergy with UV-A light irradiation. Likewise, the nano-compounds object of the present patent are neither genotoxic nor mutagenic.

In a third aspect, the invention refers to a pharmaceutical composition with cytotoxic activity for cancer treatment that comprises a functionalized multi-walled carbon nano-compound and Anatase phase $TiO_2$ (FMWCNTs) and/or functionalized, Anatase phase $TiO_2$ and folate ($TiO_2$-FMWNTs-Folate) and one or more pharmaceutically acceptable excipients to adapt the pharmaceutical liquid, solid, or heterodisperse form.

Said composition can be formulated with one or more pharmaceutically acceptable excipients for oral administration in pharmaceutical liquid or solid forms; for topical administration in heterodisperse forms (W/O creams, O/W creams, gels, and ointments, among others) and for parenteral or rectal administration. The compositions of the invention can be administered orally, rectally, parenterally, topically, intravaginally, bucally, or as a nasal or oral spray to humans and other mammals.

An additional aspect divulges a method for cancer treatment that comprises administration of a therapeutically effective amount of a functionalized multi-walled carbon nano-compound and Anatase phase $TiO_2$ (FMWCNTs) and/or functionalized, Anatase phase $TiO_2$ and folate ($TiO_2$-FMWNTs-Folate) concomitantly with irradiation with UV-A light in localized manner over cancerous tissue.

Example 1. Synthesis of Anatase Phase Titanium Dioxide

Figure 1:
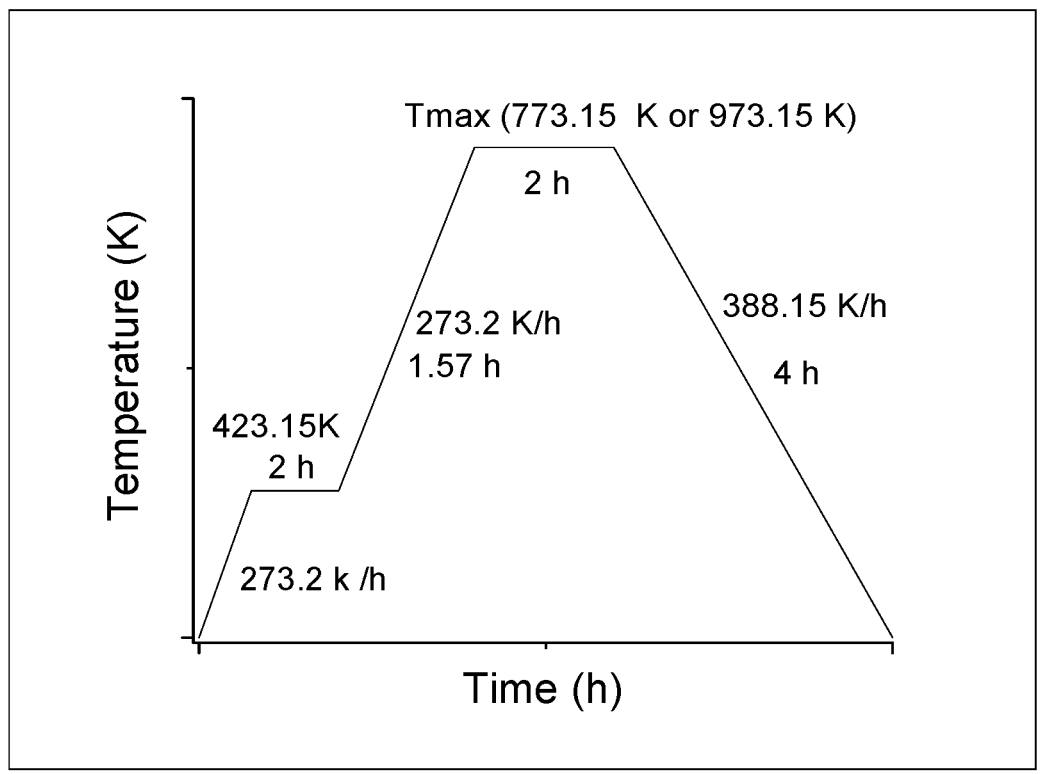
FIG. 1 shows a scheme of the temperature ramp used during the synthesis process of the invention to obtain Anatase phase $TiO_2$.

To synthesize the $TiO_2$ nanomaterial, the following procedure is carried out: add TBT (titanium tetrabutoxide) at 99% in anhydrous ethanol and shake in ultrasonic bath for 3 min at room temperature. Then, add water and shake for 10 min in ultrasound equipment. The percentages of the precursor (TBT) with the ethanol and water reagents are at 76.34%, 21.96%, and 1.7% in volume, respectively. The sol obtained is brought to a desiccator for 72 h, permitting the condensation reaction. Thereafter, it is dried at 100° C.; it is pre-calcined at 200° C. and calcined at 500° C., according to the diagram in FIG. 1, to obtain Anatase phase $TiO_2$.

Example 2. Synthesis of Multi-Walled Carbon Nanotubes Comprising Anatase Phase Titanium Dioxide To obtain this nanomaterial of titanium dioxide-multilayered carbon nanotubes ($TiO_2$-MWCNTs), of between 1 and 5 wt % of multi-walled carbon nanotubes (MWCNTs) were used without functionalizing, with diameters from 20 to 30 nm, length from 10 to 30 μm, ash content below 1.5%, and purity above 95%. The proportion of nanotubes used in the samples is 2.1% in mass. The MWCNTs are dispersed in anhydrous ethanol (Mallinckrodt) in an ultrasonic bath for 3 min and at room temperature.

Then, TBT (Aldrich 99%) is added and shaken for another 3 min; thereafter, deionized distilled water is added slowly (10 min). During the process, hydrolysis and poly-condensation are generated upon interaction of the precursor (TBT) with the ethanol and water reagents, in 76.34%, 21.96%, and 1.7% in volume, respectively. The sol obtained is brought to a desiccator for 72 h, permitting the condensation reaction. It is, then, dried at 100° C., pre-calcined at 200° C., and calcined at 500° C., according to the diagram in FIG. 1, to obtain Anatase phase $TiO_2$.

Example 3. Synthesis of Functionalized Multi-Walled Carbon Nanotubes Comprising Anatase Phase Titanium Dioxide and Folate ($Tio_2$-Fmwnts-Folate)

To obtain this nanomaterial of functionalized multi-walled carbon nanotubes, Anatase phase $TiO_2$, and folate ($TiO_2$-FMWNTs-Folate), the material obtained in example 2 is used. Initially, 30 mL of dicyclohexylcarbodiimide and 30 mL of N-hydroxysuccinimide (Aldrich chemistry) are shaken in a 1:1 ratio with a concentration 0.05 M in DMSO for 5 min in ultrasound equipment. Add 1.5 g of the material from example 2 and agitate for 1 h in ultrasound; then, add 0.03 g of folic acid (FA) and agitate for 45 min in ultrasound. Thereafter, shaken on a plate for 6 h and centrifuged; remove the supernatant and dry for 1 h at 100° C. The end result is a nanomaterial of $TiO_2$-FMWCNTs-Folate.

Example 4. Cytotoxic Activity of the Nano-Compounds of the Invention Against Tumor and Non-Tumor Cell Lines The cytotoxic activity was evaluated in two cell lines, one of (HeLa) human cervical neoplastic cells, and another of normal CHO cells obtained from the cell line bank of the ATCC. Cytotoxicity was evaluated through LDH determination, according to formula:

$$\% \text{ of cytotoxicity} = \frac{\text{Sample Reading } (CEM) - Lowcontrol}{Highcontrol - Lowcontrol}$$

Where CEM is the calculation of the average absorbance values of the tests in triplicate.

The treatments were evaluated in two concentration or dosage levels: 100 and 200 μg/mL. The nano-compounds evaluated were: anatase phase titanium dioxide (A), multi-walled carbon nanotubes comprising anatase phase titanium dioxide ($TiO_2$-MWCNTs), and (B) multi-walled carbon nanotubes comprising anatase phase titanium dioxide and folate ($TiO_2$-FMWNTs-Folate) (C); triton X-100 at 2% was used as positive control.

Figure 2:
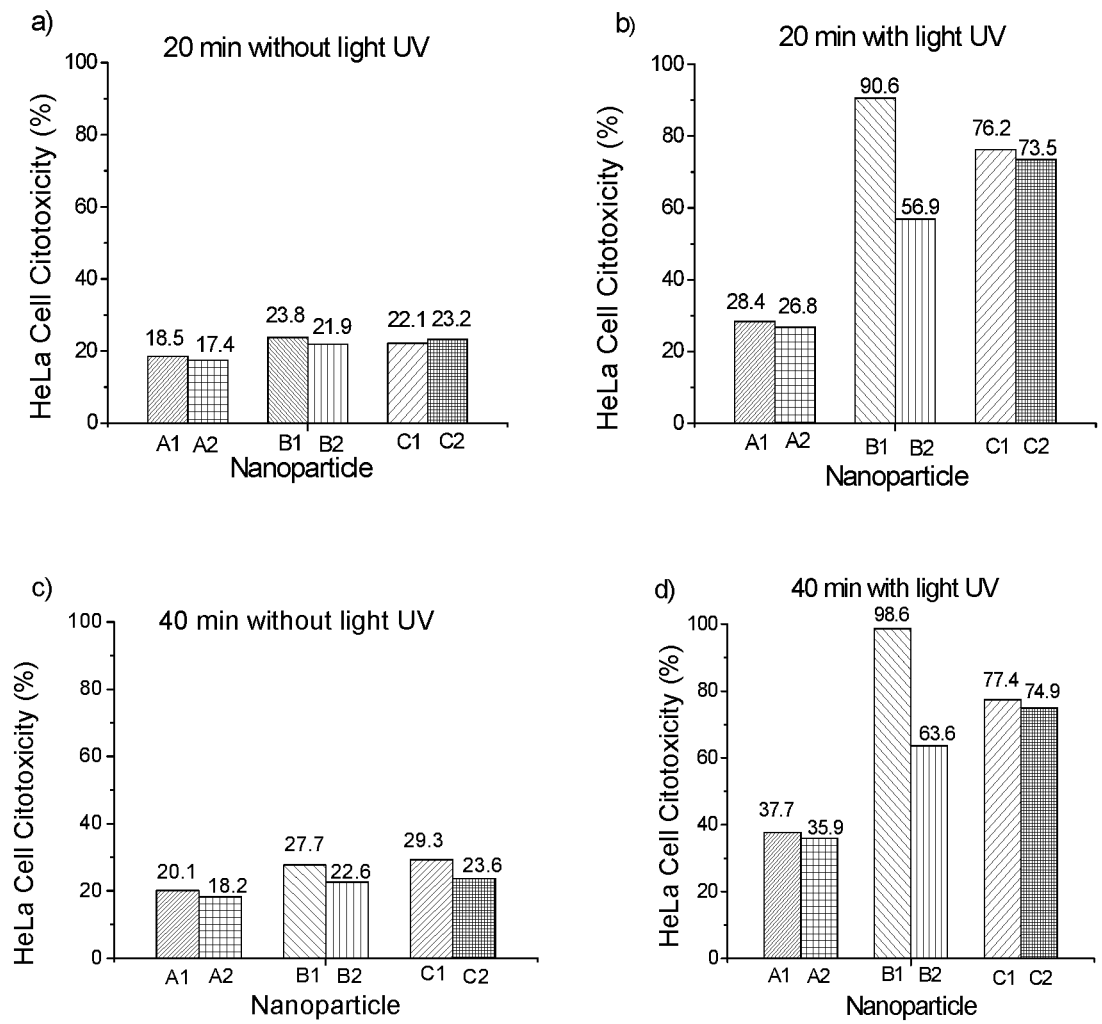
FIG. 2 shows the cytotoxicity of the nano-compounds upon a cervical cancer (HeLa) cell line. a) 20 min without UV, b) 20 min with UV, c) 40 min without UV, d) 40 min with UV.

Treatments were evaluated with or without UV irradiation for a time of 20 to 40 min. FIG. 2 shows the cytotoxicity percentage of the HeLa cell line (dead cells with respect to the control) for each of the treatments and conditions evaluated. It is noted that the highest cytotoxicity percentage was 98.6% corresponding to the effect of the B1 nano-compound ($TiO_2$-FMWCNT) at a concentration of 200 μg/ml, exposed to UV radiation for 40 min. It can also be noted that the cytotoxic effect of the nano-materials increases over time (higher effect at 40 min); likewise, cytotoxicity increases through co-treatment with UV radiation.

Similarly, it is noted that the C1 nano-compound (200 μg/ml of $TiO_2$-FMWCNT-folate) has an increase in the significant cytotoxic percentage when treatment time increases from 20 to 40 min without exposure to UV light.

FIG. 3 shows that the cytotoxicity percentage values of these non-tumor CHO cells are negative, from where it is inferred that there is no cytotoxic effect of the nano-compounds upon normal CHO cells. It is also evidenced that no treatment below the treatment conditions is cytotoxic with or without exposure to UV light, which shows the specificity of the nano-compound's cytotoxic effect.

Example 5. Genotoxicity and Mutagenicity of the Invention's Nano-Compounds

The genotoxicity tests were conducted with EBPI SOS-CHROMOTEST™ and mutagenicity tests were conducted with EBPI's Muta-ChromoPlate™.

The EBPI SOS-CHROMOTEST™ is a practical approach for detection of genotoxic activity and genotoxic materials in environments, like: water, sediments, air, chemicals, foods, cosmetics, and biological fluids. Genotoxic materials can be dangerous due to the ease with which they induce cancerous transformations to normal cells. The readings permitted concluding that the wells contain bacteria, but not genotoxins, evidencing production of enzymes not connected to activation of the SOS gene repair complex.

The EBPI Muta-ChromoPlate™ kit is a convenient approach for detection of mutagenic activity and of mutagenic materials in environments, like: water, sediments, air, chemicals, food components, cosmetics, and biological fluids. Mutagenic materials can be dangerous due to the ease with which they induce cancerous transformations to normal cells.

Results are shown in Table 1, where it is noted that none of the nano-materials of the invention induce significant mutagenotoxicity after 5 days of culture.

TABLE 1

Mutagenotoxicity detected at days 3, 4, and 5 for the nano-compounds of the invention

| Treatment | Day 3 | Day 4 | Day 5 |
| --- | --- | --- | --- |
| Target | 0 | 0 | 0 |
| Background | 5 | 9 | 11 |
| Positive control | 34 | 89 | 96 |

TABLE 1-continued

Mutagenotoxicity detected at days 3, 4, and 5 for the nano-compounds of the invention

| Treatment | Day 3 | Day 4 | Day 5 |
| --- | --- | --- | --- |
| Anatase phase $TiO_2$ | 10 | 12 | 13 |
| $TiO_2$-MWCNTs | 7 | 15 | 16 |
| $TiO_2$-FMWNTs-Folate | 5 | 6 | 8 |

Although the present invention has been described with the preferred embodiments shown, it remains understood that the modifications and variations that conserve the spirit and reach of this invention are understood within the reach of the claims included.

The invention claimed is:

1. A nano-compound comprising folate functionalized $TiO_2$ multi-walled carbon nanotubes, wherein the $TiO_2$ and the folate are covalently attached to the multi-walled carbon nanotubes.

2. The nano-compound of claim 1, wherein the $TiO_2$ functionalized multi-walled carbon nanotubes have diameters of between 20 to 30 nm and length of between 1 to 30 µm.

3. A pharmaceutical composition comprising the nano-compound from claim 2 and a pharmaceutically acceptable diluent.

4. A process for synthesis of the nano-compound of claim 1 that comprises the stages of:
dispersing between 1 and 5% p/p of functionalized multi-walled carbon nanotubes in anhydrous $C_{1-4}$ alcohol in an ultrasonic bath with a frequency of 20 kHz for a time of between 1 and 5 min at a temperature of between 10 and 20° C.; wherein said nanotubes have a length of between 1 and 30 µm, a diameter of between 20 and 30 nm, a length of 10 to 30 µm, ash content below 1.5%, and purity above 90% to form a mixture;
adding titanium tetrabutoxide ($Ti(OBu)_4$) at 99% purity and shaking for 1 to 5 min at a temperature of between 10 and 20° C.;
adding deionized distilled water at a rate of between 10 and 20 ml/min to obtain a solution of $C_{1-3}$ alcohol: water with a concentration of between 70 and 90% of $C_{1-3}$ alcohol and 10 to 30% of water by volume;
allowing the mixture to rest in a desiccator at a temperature of between 10 and 20° C. for 24 to 96 h to permit a condensation reaction to occur;
heating the mixture at a rate of between 0.01 and 0.1° C./min to a temperature of between 100 and 250° C. for 1 to 3 h;
heating the mixture at a rate of between 0.01 to 0.1° C./min to a temperature of between 450 and 550° C. and maintaining this temperature for 1 to 3 h;
cooling the mixture to a temperature of between 10 and 20° C. at a rate of between 100 to 150° C./min to produce $TiO_2$-FMWNTs;
separately mixing dicyclohexylcarbodiimide and N-hydroxysuccinimide in a 1:1 ratio at a concentration of 0.01 to 0.1 M in DMSO for a time of between 3 and 7 min in ultrasound equipment to form a mixture;
combining $TiO_2$-FMWNTs with the mixture of dicyclohexylcarbodiimide and N-hydroxysuccinimide made in the previous step;
shaking the combination made in the above step in an ultrasonic bath for a time of between 30 and 90 min at a temperature of between 10 and 20° C.;
adding folic acid to the mixture of $TiO_2$-FMWNTs and dicyclohexylcarbodiimide and N-hydroxysuccinimide in DMSO;
shaking the mixture of the above step in ultrasonic bath;
centrifuging the mixture of the above step and removing the supernatant.

5. A method for the treatment of cancer comprising administering a therapeutically effective amount of the nano-compound from claim 1 concomitantly with UV-A type ionizing radiation in a localized manner over cancerous tissue.

6. A method for the treatment of cancer comprising administering a therapeutically effective amount of the nano-compound from claim 2 concomitantly with UV-A type ionizing radiation in a localized manner over cancerous tissue.

* * * * *